(12) United States Patent
Machado et al.

(10) Patent No.: US 9,186,095 B2
(45) Date of Patent: Nov. 17, 2015

(54) EVALUATION OF MOVEMENT DISORDERS

(71) Applicant: THE CLEVELAND CLINIC FOUNDATION, Cleveland, OH (US)

(72) Inventors: Andre Machado, Beachwood, OH (US); Jay L. Alberts, Chagrin Falls, OH (US); Cameron McIntyre, Cleveland, OH (US); David Schindler, Russell, OH (US)

(73) Assignee: The Cleveland Clinic Foundaton, Cleveland, OH (US)

( * ) Notice: Subject to any disclaimer, the term of this patent is extended or adjusted under 35 U.S.C. 154(b) by 258 days.

(21) Appl. No.: 14/024,368

(22) Filed: Sep. 11, 2013

(65) Prior Publication Data

US 2014/0073994 A1   Mar. 13, 2014

Related U.S. Application Data

(60) Provisional application No. 61/699,435, filed on Sep. 11, 2012.

(51) Int. Cl.
*A61B 5/11* (2006.01)
*A61B 5/00* (2006.01)

(52) U.S. Cl.
CPC .................. *A61B 5/11* (2013.01); *A61B 5/1124* (2013.01); *A61B 5/6897* (2013.01); *A61B 5/0022* (2013.01); *A61B 5/4082* (2013.01); *A61B 2562/0219* (2013.01)

(58) Field of Classification Search
CPC ................... A61B 5/11; A61B 5/1101; A61B 5/1124–5/1127; A61B 5/103
See application file for complete search history.

(56) References Cited

U.S. PATENT DOCUMENTS

| 5,772,611 | A | 6/1998 | Hocherman |
| 7,621,908 | B2 | 11/2009 | Miller |
| 7,643,882 | B2 | 1/2010 | Boston |
| 7,647,117 | B2 | 1/2010 | Bauhahn |
| 2004/0140962 | A1 | 7/2004 | Wang et al. |

(Continued)

FOREIGN PATENT DOCUMENTS

| EP | 1441279 A2 | 7/2004 |
| WO | 2011141734 A1 | 11/2001 |
| WO | 2008037260 A2 | 4/2008 |
| WO | 2011063248 A1 | 5/2011 |

OTHER PUBLICATIONS

International Search Report and Written Opinion, mailed Mar. 18, 2014, pp. 1-11.

(Continued)

*Primary Examiner* — Max Hindenburg
(74) *Attorney, Agent, or Firm* — Tarolli, Sundheim, Covell & Tummino LLP (57) ABSTRACT

This disclosure relates to a system and method to evaluate movement disorders. A movement data aggregator can combine data from a plurality of sensors into an aggregate movement data describing multi-dimensional movement of a handheld device. A calculator to compute an indication of a movement disorder based on the movement vector data and user input data, the user input data being generated in response to physical interaction between the handheld device and a human machine interface of a computing device/machine that is separate from the handheld device. In some examples, the handheld device can communicate with computing device via a wireless interface.

27 Claims, 6 Drawing Sheets

(56) References Cited

U.S. PATENT DOCUMENTS

2008/0248871 A1   10/2008   Szturm et al.
2010/0152622 A1    6/2010   Teulings
2010/0331807 A1   12/2010   Whitehurst et al.

OTHER PUBLICATIONS

Mera et al., Feasibility of Home-Based Automated Parkinson's . . . , Jnl of Neuroscience Methods 203 (2012), pp. 152-156.
Hoffman et al., Objective Measure of Upper Extremity Motor Impairment in Parkinson's Disease With Inertial Sensors, 33rd Annual Intl. Conference of the IEEE EMBS, 2011.

EVALUATION OF MOVEMENT DISORDERS

CROSS-REFERENCE TO RELATED APPLICATION

This application claims the benefit of U.S. Provisional patent application No. 61/699,435, filed on 11 Sep. 2012 and entitled EVALUATION OF MOVEMENT DISORDERS, the entire contents of which is incorporated herein by reference.

TECHNICAL FIELD

This disclosure relates to evaluation of movement disorders.

BACKGROUND

There are various neuromotor and neurocognitive disorders including Alzheimer's disease, Parkinson's Disease (PD), and progressive supranuclear palsy to name a few. Neuromotor and neurocognitive disorders affect motor function, cognitive function or both. In order to properly treat many neuromotor and neurocognitive disorders, it is desirable to better understand or classify an individual's condition. Accordingly, a variety of tests have been developed for various types of diseases. For example, one scale for assessing a patient's Parkinson's disease is the Unified Parkinson's Disease Rating Schedule (UPDRS). Various other tests exist that are utilized by a clinician to help the clinician categorize a patient's disorder.

SUMMARY

This disclosure relates to evaluation of a movement disorder.

In one example, a system can include memory to store computer executable instructions and data. A processor can be configured to access the memory and execute the computer executable instructions. The instructions can include a data aggregator to combine motion and position data from a plurality of sensors into an aggregate movement vector data describing multi-dimensional movement of a handheld device. The aggregate movement vector data can be converted into relative movement data corresponding to a reference frame of a human machine interface, the human machine interface being separate from the handheld device. A disorder calculator can compute an indication of a movement disorder based on the relative movement data and user input data that is stored in the memory. The user input data can be generated in response to user interaction between the handheld device and the human machine interface.

In another example, a method can include receiving, via a communications link, motion and position data based on motion and position sensed by sensors of a handheld device during at least one predetermined task. The motion and position data can be combined to provide aggregate movement data describing multi-dimensional movement of the handheld device. The aggregate movement data can be converted into relative movement data corresponding to position and motion of the handheld device with respect to a reference frame of a human machine interface that is separate from the handheld device. User input data can be stored in response to user interactions detected by the human machine interface during the at least one predetermined task. An indication of at least one movement disorder can be computed based on the relative movement data and the user input data.

DETAILED DESCRIPTION

This disclosure provides a system, method and apparatus to facilitate evaluation of movement disorders.

In some examples, a system can include a handheld device configured to interact with a human machine interface (HMI) of a computing device (e.g., a touchscreen or other display). The handheld device can be implemented an active stylus that includes a plurality of sensors (e.g., accelerometer, gyroscope and/or magnetometer) that provide a kinematic monitoring system. Force sensing can also be implemented, as disclosed herein. The sensors thus can provide motion and position data for the handheld device, including during one or more predetermined tasks involving user interactions with the HMI. The HMI can thus record user interaction and store them in memory along with corresponding motion and position data for each task being performed. The motion and position data can be combined into an aggregate movement vector data describing multi-dimensional movement of the handheld device. The aggregate movement vector data further can be converted into relative movement data corresponding to a reference frame of the HMI (e.g., a display) and more specifically relative to the a given target that can be displayed on the HMI. The computing device can thus be programmed to compute an indication of one or more movement disorders based on the relative movement data and user input data, which can be collected over one or more tasks for a given test interval. Test results and test data can be obtained and evaluated over any number of tests, which can be utilized to ascertain an indication of variability for the patient's condition.

As disclosed herein, the test results can be communicated to one or more providers. This can be done by simply reviewing the results on the computing device or the results can be sent to the provider(s) via a network connection. The test results for one or more subjects, for example, can be stored in a database in a server for further analysis and comparison. Additionally, in cases where the subject includes an implantable stimulation apparatus (e.g., configured to provide deep brain stimulation or the other stimulation therapies), the provider and/or computer implemented methods operating remotely (e.g., in a server or another remote computer) or within the computing device that provides the HMI can be programmed to set one or more stimulation parameters based on the indication of one or more movement disorders that have been computed. For instance, test results for multiple tasks completed over a different time intervals (e.g., over a period of a day or a given week) can be evaluated to set one or stimulation parameters.

Figure 1:
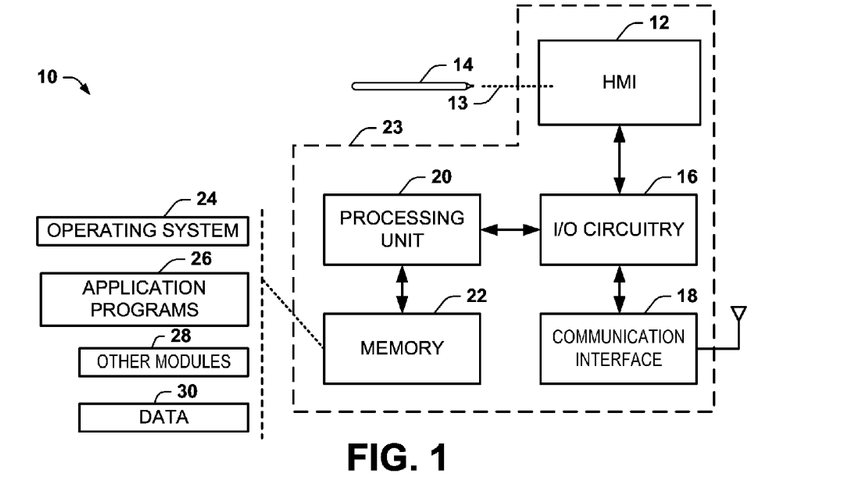
FIG. 1 depicts an example of a system that can be implemented to evaluate a movement disorder.

FIG. 1 depicts an example of a system 10 that can be configured for evaluation of movement disorders. The system 10 includes an HMI 12 (e.g., a display/touchscreen) that a user, such as patient, can employ to interact with the system 10. The HMI 12 can be implemented as a touchscreen interface that is configured to sense contact, such as via capacitive, resistive or surface acoustic wave technologies. The system 10 can also include a handheld device 14 that is separate from and moveable relative to the HMI. For example, the handheld device 14 can be implemented as a stylus, such as an active stylus that includes one or more sensors (see, e.g., FIG. 3).

As an example, a user can employ a handheld device 14 to perform a series of one or more tasks that involve physical movement of the handheld device relative to the HMI 12. The tasks can also involve physical interaction between the handheld device 14 and the HMI 12, such as the example tasks disclosed herein. The physical interaction between the handheld device 14 and the HMI 12 is demonstrated schematically by dotted line 13.

The computing system 10 can include input/output (I/O) circuitry 16 configured to communicate data with various input and output devices coupled to the computing system 10. In the example of FIG. 1, the I/O circuitry 16 is connected to communicate with the HMI 12 and a communication interface 18. The communication interface 18 can be configured for wireless communication with corresponding wireless communication interface of the handheld device 14, such as via an antenna 32. In this way, acquired movement data and other data can be communicated wirelessly from the handheld device 14 to the communication interface 18. As an example, the communication interface 18 can be configured to provide for short-range wireless communication, such as Bluetooth, WiFi or the like. Depending on the wireless communication protocol, the handheld device 14 can register with the communication interface 18 of the computing system 10 to facilitate collection of movement data from the handheld device.

The movement and other data can be communicated from the handheld device 14 to the communication interface 18 in real time. For example, real time communication of such data can enable control functions (e.g., stored in memory 22) to control the HMI and corresponding tasks in a patient specific manner. For instance, the size and difficulty can be increased if the movement data and/or other patient information (e.g., age, prior test results or the like) indicate an increased ability for the given subject. In contrast, if the movement data or other data indicates a decreased ability, the difficulty and/or complexity of the test can be decreased to such reduced abilities of the subject. In other examples, the data may be communicated in batch processes following a test, such as at predetermined scheduled times or in response to activating a data collection process (in response to a user input—locally or remotely entered).

The computing system 10 can also include a processing unit 20 and memory 22. The memory 22 can be a non-transitory memory configured to store machine readable instructions and/or data. The memory 22 could be implemented, for example as volatile memory (e.g., RAM), non-volatile memory (e.g., a hard disk, flash memory, a solid state drive or the like) or combination of both. The processing unit 20 (e.g., a processor core) can be configured in the system for accessing the memory 22 and executing the machine-readable instructions. The processing unit 20, I/O circuitry 16, memory 22, communications interface 18 and HMI 12 can be implemented to provide a computing apparatus 23, such as a tablet computer, a notebook computer, a desktop machine or the like.

By way of example, the memory 22 can store a variety of machine readable instructions and data, including an operating system 24, one or more application programs 26, other program modules 28, and program data 30. The operating system 24 can be any suitable operating system or combinations of operating systems, which can vary from system to system. The application programs 26, other program modules 28, and program data 30 can cooperate to provide motor and cognitive testing via the computing apparatus 23, such as disclosed herein. Additionally, application programs 26, other program modules 28, and program data 30 can be used for computation of an indication of motor, cognitive or a combination of motor and cognitive functions of a patient based on the testing data, including data obtained via the handheld device in conjunction with data obtained by the HMI in response to user inputs, such as disclosed herein.

A user may enter commands and information into the computing system 10 through one or more user input devices, such as the HMI 12 or other user input devices (e.g., a mouse, microphone, a keyboard, a joystick, a game pad, a scanner, or the like. Such other user input devices (not shown) could be coupled to the computing system via the I/O circuitry 16 via a physical connection or wirelessly to the communications interface 18.

As a further example, the communications interface 18 can be configured to communicate with an implantable stimulation apparatus (e.g., an implantable pulse generator (IPG)). Such communication can be via a wireless communications link and/or a physical communications link (e.g., electrically conductive or optical link), which can vary depending on the type and capabilities of the stimulation apparatus. For example, the application programs 26 can be configured to program one or more control parameters of the implantable stimulation apparatus. The programming can be an automated process implemented solely by machine-readable executable instructions, a manual process requiring a user input from an authorized user (e.g., entered directly into the computing apparatus 23 or remotely entered and communicated to the computing apparatus), or a semi-automated process that involves both an automated method and one or more manual inputs (e.g., an approval entered by an authorized health care provider). The programming can be performed while the stimulation apparatus is implanted in the patient's body. Such programming can also be performed prior to implantation of the stimulation apparatus.

Figure 2:
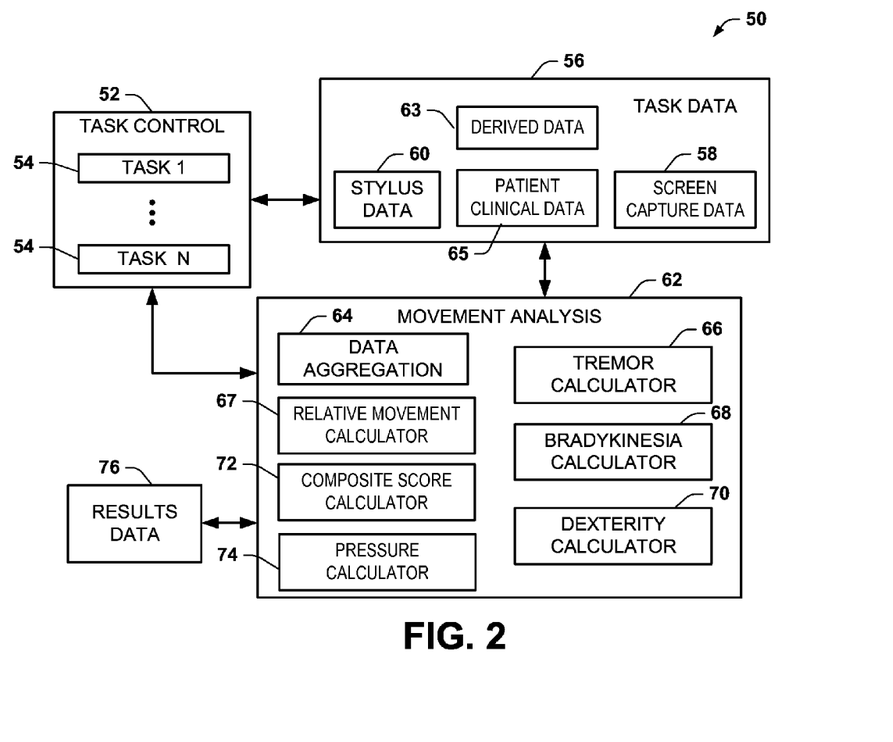
FIG. 2 depicts an example of machine readable instructions that can be programmed to evaluate motor disorders.

FIG. 2 depicts an example of machine readable instructions 50 and data that can be programmed to evaluate movement disorders. The machine readable instructions 50 can be stored in the memory 22 of FIG. 1, for example. A task controller 52 can be configured to implement one or more tasks 54, demonstrated as tasks 1 though N, where N is a positive integer. Each task 54 can be programmed to provide a graphical user interface that displays graphics corresponding to a predefined test, and collects task data 56 in response to user inputs (e.g., via HMI 12 of FIG. 1) and user interactions (e.g., via the handheld device 14 of FIG. 1) during each respective task.

The task data 56 can include screen capture data 58 received in response to user input, such as can be made via a touchscreen (e.g., HMI 12 of FIG. 1). The screen capture data 58 can also include graphical and other information that is provided as part of the task and results of the task responsive to user interactions. For example, the results and other information in the screen capture data 58 can include timing information obtained during the task, such as in response to one or more user inputs. The timing information can be employed to synchronize the screen capture data for a given task with the stylus data for the same given task. The screen capture data 58 can also include a recording of the test and user interactions with the HMI for each of the tasks performed, which recording can be played by a healthcare provider or other authorized user to visualize the testing process as it actually occurred.

The task data 56 can also include stylus data 60 that includes data collected from a stylus (e.g., from handheld device 14 via the wireless communication interface 18 of FIG. 1) during each respective task. The stylus data 60 can also include timing information (e.g., a clock value) indicating timing of a given task. For example, a synchronization pulse can be sent to the handheld device (e.g., via the communications interface 18) to indicate a task is starting. This can instantiate a task timer at the device that can be utilized to provide timing information during the respective task. The timing information can be employed to synchronize the screen capture data for a given task with the stylus data for the same given task. Thus the task data can include a combination of data from disparate and separate devices (e.g., from the stylus and from the HMI) that cooperate to perform each respective task. As disclosed herein, the cooperation can include, for at least some tasks, using the stylus to interact with the HMI and provide corresponding synchronized task data.

The type of movement and interactions between the stylus and the HMI can vary from task to task. In some examples, the stylus data 60 can represent multi-dimensional movement and position of the stylus (e.g., kinematic information), such as including acceleration in one more directions, angular orientation of the stylus in one or more dimensions and magnetic field sensed along one or more directions. The stylus data 60 can also include or be used to derive data representing force or pressure resulting from physical contact between the stylus and a surface of the HMI (e.g., a touchscreen surface). The stylus data 60 can also include other information relevant to tasks or the task environment, such as timing information (e.g., timestamp applied to such data), temperature, altitude, user inputs received via user inputs at the stylus and the like.

A movement analysis function 62 can be programmed to analyze the task data acquired for each task, including the screen capture data 58 and stylus data 60. The analysis function 62 can compute an indication of a movement disorder based on the task data 56. In addition to the screen capture data 58 and the stylus data 60, the task data 56 can also include derived data 63 determined by the movement analysis. Additionally or alternatively, the task data 56 can include patient/clinical data 65 representing a condition of the patient, such as demographic (e.g., age, sex, weight) or other patient information relevant to the disorder being evaluated (e.g., when disorder was first diagnosed, severity indicators or the like).

In some examples, the task data 56—or at least portions of it—can be acquired over a plurality of different tasks, each designed to measure different motor and/or cognitive capabilities of a patient during each respective task. As disclosed herein, the measurements can involve a physical interaction between a handheld device and a human machine interface (e.g., a touchscreen) for one or more of the tasks. The measurements can also involve measuring kinematics of the handheld device itself during each task as well as measurements derived solely from the HMI in response to user inputs during each respective task.

The analysis function 62 can include a data aggregation module programmed to aggregate data acquired from the handheld device for each task into a movement vector that describes multi-dimensional motion and position of the handheld device during the respective task. For example, the stylus data 60 can be generated from a plurality of different sensors (e.g., an accelerometer, gyroscope and magnetometer) that each can provide multidimensional data associated with the kinematics of the handheld device. The stylus data 60 can include other information as disclosed herein (e.g., force or displacement of a stylus tip and the like). The data aggregation module 64 can compute the multi-dimensional movement vector to vary as a function of time during each respective task based on the task data 56 and timestamps appended to the acquired sensor data.

An example of how such data can be aggregated to calculate the multidimensional movement vector is disclosed in Appendices A-E of the above-incorporated U.S. Provisional patent application No. 61/699,435. Appendices A-E of this provisional application provide examples of mathematical procedures that can be utilized to combine the sensor data from the accelerometer, magnetometer and gyroscope into a single multi-dimensional value based on the stylus data 60 that can be provided from the respective multi-dimensional sensors implemented in the stylus. Other approaches could also be utilized to combine such the stylus data 60 for use in implementing the systems and methods disclosed herein.

Since the aggregated movement data is provided in the reference frame of the stylus itself, a relative movement calculator 67 can be programmed to convert such data into a reference frame of the HMI with which it interacts. The relative movement calculator 67 can store the converted data as part of the derived data 63. In the frame of reference of the HMI, the aggregate movement vector data during a given test can represent kinematics of the handheld device with respect to the HMI.

The movement analysis can include one or more disorder calculator programmed to compute a value representing one or more respective symptoms of movement disorders. The particular symptoms and disorders that are computed by the movement analysis 62 can be selected based the patient/clinical data. In the example of FIG. 2, the movement analysis function includes a tremor calculator 66, a bradykinesia calculator 68, a dexterity calculator 70 and a composite score calculator 72. The movement analysis can also include a pressure calculator to compute pressure sensed based on displacement information provided from a displacement sensor of the handheld device (e.g., sensor 110 of FIG. 3) during a given task. Each of such calculators 66, 68, 70, 72 and 74 can be programmed to compute a value (e.g., an index or score) corresponding to the movement or other properties detected during a given task or over a set of tasks. Such computed values can be stored as results data 74 in memory. One or more of the calculators 66, 68, 70, 72 74 may be referred to herein as a disorder calculator. The computations by each calculator 66, 68, 70 and/or 72 can further vary depending on the task being performed. Moreover, different weighting can be applied to the results of a given calculation, which can vary according to the movement the type or types of movement being evaluated in each respective task and other task data (e.g., including the patient/clinical data).

The movement analysis 62 can also integrate time-synchronized data and related calculations from various calculators to derive an indication of various symptoms. For example, the movement analysis 62 can compare stylus position and stylus tip velocity (e.g., first derivative of tablet screen position) relative to tip displacement, linear acceleration, rotational velocity, jerk (first derivative of acceleration), roll, pitch and yaw. Additionally or alternatively, movement analysis 62 can compare performance on tablet tests (e.g., incorporating time and stylus position as a measure of precision and speed) with stylus sensor data listed above. Other comparative analysis between data from the stylus and the HMI can be performed.

By way of further example, the task controller 52 can be programmed to control a procedure utilized to acquire data indicative of a plurality of movement disorder symptoms, such as including tremor (resting, postural re-emerging and action), bradykinesia and dexterity. The movement analysis functions 62 can thus evaluate the stylus data 60 and screen capture data 58 acquired over a series of tasks 54 implemented by the task controller 52 in conjunction with the derived data and the patient/clinical data 65. The following provides an example of a testing workflow corresponding to tasks 54 that can be implemented by the task controller 52 to provide a graphical user interface via the HMI and collect corresponding stylus data 60 and screen capture data 58.

The testing workflow may begin by showing an instructional video of the tasks to the user, such as can be presented to the subject via the HMI (e.g., on a touchscreen). During the presentation of the instructional video as well as during the tasks, a camera of the tablet can be used to capture images that can be later evaluated by the clinician (or the patient) to assess compliance with the instructions. For some tablet devices, the tablet may have to be rotated so that the camera is on the right for a right upper extremity task and on the left for a left upper extremity task. Instructions can be provided to the patient advising on the correct orientation of the tablet depending on task requirements.

To begin a first task 54, the stylus can be set at a predetermined position on a table, such as located between the patient and the tablet/computer. The distances have to be pre-determined and may require a template to be provided with the stylus. For example, a table mat, a sheet of paper or other layout article can be provided with a pre-drawn layout of where the patient should be, where the tablet should be and where the stylus should be set for each task. Each task can utilize the same layout of stylus and tablet or different layouts can be used for different tasks.

Once the stylus and tablet have been positioned at their respective starting positions, a first task (Task 1) can begin, such as for collecting data for evaluating bradykinesia/dexterity. The Task 1 function can be programmed to provide a "go" message, which starts the internal clock in the tablet for the respective task and provides a synchronization pulse to the handheld device (e.g., via the communications interface 18 of FIG. 1). In this example task, the task function 54 can be programmed to present a graphics and instructions to the user. For instance, the screen can be divided in four quadrants with two orthogonal lines. As instructed by the Task 1 function 54, the patient picks up the stylus from the pre-set position on the table and taps a given quadrant with the stylus corresponding to physical interaction between the stylus and the tablet. For instance, the given quadrant can be differentiated from the other quadrants, such as by blinking or lighting or otherwise distinguishing it from the other quadrants. During movement of the stylus, stylus data can be collected corresponding to multi-dimensional motion of the stylus detected by respective sensors (e.g., accelerometer, gyroscope and magnetometer). Once the tap is accomplished, another quadrant lights and the patient has to tap that quadrant. The task function 54 can be programmed to repeat this test in random fashion a plurality of times, and the time between cue and tap is measured each time.

During each test, the HMI (e.g., the touchscreen) can capture if the patient is removing the stylus off the screen to go to the other quadrant (as instructed) or merely dragging the stylus on the screen from quadrant to quadrant. Such information can be stored as part of the screen capture data 58. If the user does not remove the stylus from the screen, the task controller can be programmed to generate an instructional message to the patient. Additionally or alternatively, a video of that component of the task can be repeated for the patient to demonstrate and instruct the patient on the correct way to perform the test.

A second task (Task 2) 54 can be programmed to begin upon completion of the preceding task. The task can include presenting via the display instructions and/or a video or image of how to hold the stylus in his/hers hand in a resting position over his/hers lap. When the patient gets to the correct position, the patient can activate a button or switch of the stylus. In response, the task 54 can begin recording of one or more components of the stylus data 60, such as acceleration data (e.g., for measuring tremor characteristics). For instance, the Task 2 function 54 can generate a message on the display indicating that the patient should stay at rest and this lasts for a predetermined time period (e.g., 60 seconds). This interval can be programmable and thus be adjusted to more or less time, depending on patient specific tremor characteristics. In this example, the accelerometer of the stylus can measure acceleration of the patient during this predetermined time period, based on which data the tremor calculator 66 can compute an indication of resting tremor for the patient over one or more such tests.

As a further example, another task (Task 3) function 54 can be programmed to collect parameters that can provide a measure of postural or re-emerging tremor. For instance, the Task 3 function 54 can generate a message (e.g., on the display and/or audio) instructing the patient to take the stylus, bring it into contact with the screen and hold the stylus in a specified position against the screen. A picture can be shown of how the subject should position himself/herself in relation to the tablet and how the elbow should be positioned (off the table). A countdown can be shown indicating to the patient how long to hold this position, such as about 30-60 seconds, for example. During this task, postural or re-emerging tremor may occur and the patient can be instructed to try to keep the stylus against the screen as firmly as possible.

During this test, the accelerometer of the stylus can measure tremor, such as based on fast Fourier Transform analysis of the multi-dimensional accelerometer data. Additionally, the pressure applied against the screen can also be measured, such as by the touchscreen HMI and/or by a pressure or displacement sensor implemented at the tip of the stylus. The Task 3 function 54 can also collect data via the touchscreen including a count for the number of (non-intentional) hits that will occur against the screen due to severe tremor. In some examples, the intensity (e.g., measure of force) of each hit against the screen can also be measured. Such force per hit (or a force profile over time for each hit) can be measured by sensors at the touchscreen and/or by a displacement/pressure sensor of the stylus.

Another task (Task 4) 54 can be programmed to measure another feature of tremor. The Task 4 function 54 can be programmed to instruct the subject (e.g., via audio and/or video images) to bring an edge or blunt tip of the stylus to the tip of the subject's chin and back to the screen multiple times. The patient can be instructed to push a stylus button each time that the stylus touches the chin or each time that it is close to the chin, in case the patient cannot accurately touch the chin due to excess tremor. The touchscreen captures the time when it is touched by the stylus so that the software can assess the speed of the back and forward movements. Acceleration and jerk associated with the back and forth movements can also be determined by performing time derivatives on the movement data that is acquired. The time when the stylus button is activated can also be stored as part of the Task 4 data (e.g., stylus data) as well as movement data from one or more motion sensors during such task.

Another task function (Task 5) 54 can be programmed to implement a test to collect data to provide a measure of dexterity. For instance, the Task 5 function can provide instructions to the patient to tap a quadrant of the screen as many times as that quadrant blinks, and in the same speed as it blinks. The task function 54 can control the number of times and the rate at which the quadrants will blink and/or the size of the quadrants relative to the screen size. The control can be implemented randomly or it can be patient-specific based on patient/clinical data for the subject. For example, the quadrants can blink a number of times, such as from one to five times and in a determined (or random) order, forcing the patient to move the stylus (again, without dragging) from one quadrant of the screen to the next as the quadrants blink. In some cases, the quadrants may only blink once and then move to another quadrant but in some cases it will blink a few times before another one blinks a few times, adding to the difficulty of the task. The task function 54 can control the difficulty of the test depending on the patient's abilities, as measured by the touchscreen. For example, the task can have a flow from low difficulty (slow single blinks) to high difficulty (fast multiple blinks) over the course of the task.

Figure 3:
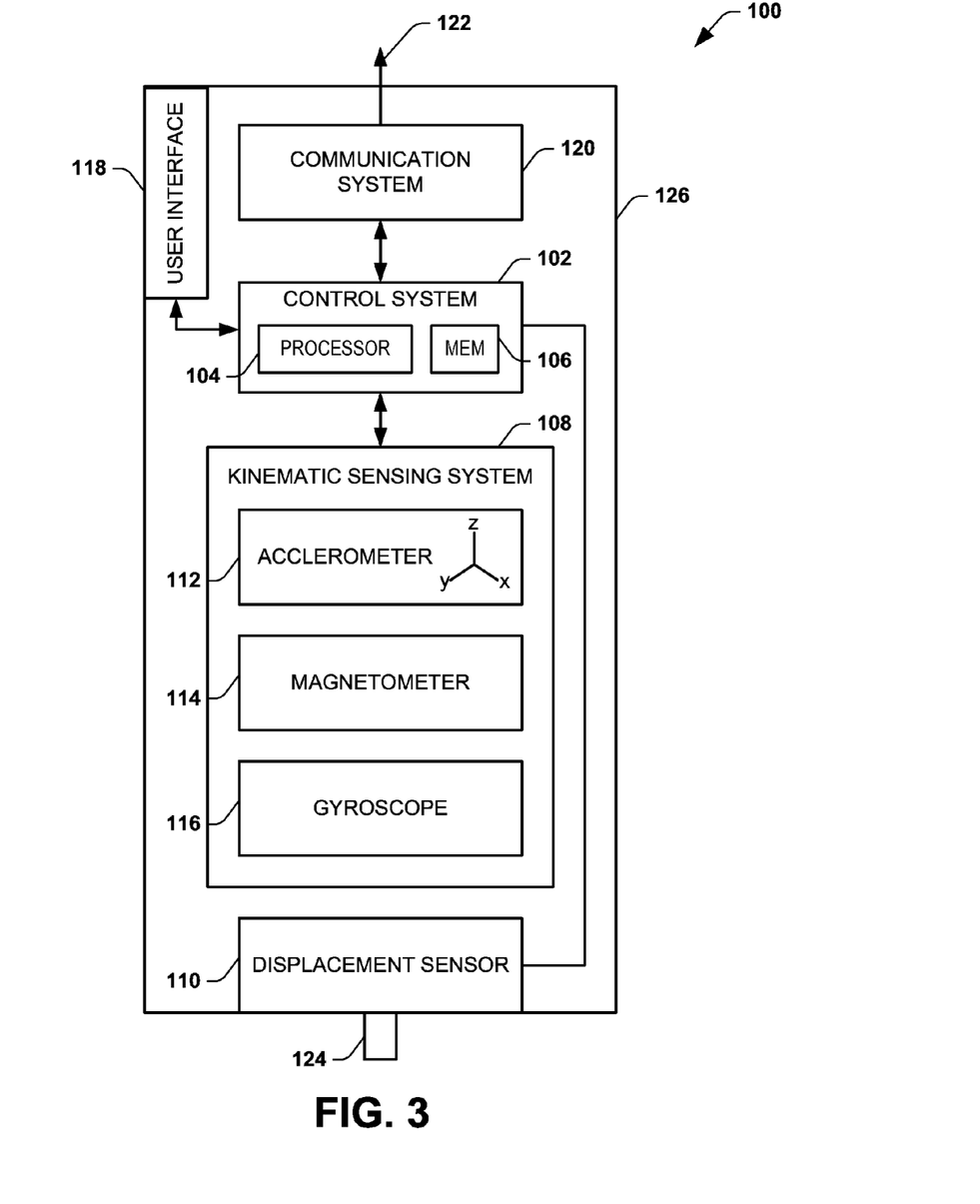
FIG. 3 depicts an example of a handheld device that can be utilized to obtain kinematic information.

FIG. 3 depicts an example of a handheld device 100 that can be utilized in the systems and methods disclosed herein for evaluating movement disorders. The device 100 can be an active stylus that is moveable relative to an HMI, such as a touchscreen display of a tablet or other computing apparatus (e.g., the apparatus 23 of FIG. 1). The device 100 can include a control system 102 configured to control operation of the device and acquisition of data from sensors. The control system 102 can include a processor 104 and memory 106. The memory 106 can be a non-transitory medium configured to store machine readable instructions and data, including acquired data and user input data collected at the device. The processor 104 can access the memory 106 and execute the instructions to control sensing functions associated with a kinematic sensing system 108 and a displacement sensor 110. The processor can also control functions and methods in response to user input received via a user interface 118 (e.g., a button or switch). The processor 104 can also be coupled to a communication system 120 for controlling communication of data to a remote computing machine (e.g., the computing system 10 of FIG. 1). As disclosed herein, the data can be sent in real time to the computing system while tasks are being performed. Alternatively, the data processor can send the data in a batch process or periodically at other scheduled timing intervals. The data communicated via the communication system 120 can include sensor data as well as information derived from the sensor data based on other methods stored in the memory 106 that are executed by the processor 104.

In the example of FIG. 3, the kinematic sensing system 108 can be configured to sense kinematics of the device with a plurality (e.g., nine) degrees of freedom. The kinematic sensing system 108 can include an accelerometer 112, a magnetometer 114 and a gyroscope 116. For example, the accelerometer 112 can include three accelerometers having respective orthogonal axes of sensitivity as to provide outputs representing acceleration along each axis of sensitivity, corresponding to multidimensional acceleration data.

As one example, the accelerometer 112 can be a three-axis accelerometer configured to measure the static acceleration of gravity in tilt-sensing applications, as well as dynamic acceleration resulting from motion or shock. Additionally, the Its high resolution (4 mg/LSB) may enables measurement of inclination changes less than 1.0°, for example. The accelerometer 112 may provide various sensing functions, such as activity and inactivity sensing to detect the presence or lack of motion and if the acceleration on any axis exceeds a user-defined level. The accelerometer 112 can also sense tapping (e.g., single and double taps) on a surface, such as a touchscreen, as well as sense free-fall if the device is falling. These and other sensing functions can provide output data. An example accelerometer is the ADXL345 digital accelerometer commercially available from Analog Devices. Of course, one or more other accelerometers could be utilized.

The magnetometer 114 can be configured to detect magnetic fields along three orthogonal axes. The magnetometer 114 can include anisotropic, directional sensors feature precision in-axis sensitivity and linearity. These magnetometric sensors can have a solid-state construction with low cross-axis sensitivity and be configured designed to measure both the direction and the magnitude of Earth's magnetic fields. An example magnetometer is the HMC5883L 3-axis digital compass IC commercially available from Honeywell International Inc. Of course other magnetometers could be utilized.

The gyroscope 116 can be configured to sense orientation of the device along three orthogonal axes. The gyroscope can provide gyrometer output data corresponding to orientation of the device 100 along three orthogonal axes. The gyroscope can be implemented as 3-axis MEMS gyro IC, such as including three 16-bit analog-to-digital converters (ADCs) for digitizing the gyro outputs, a user-selectable internal low-pass filter bandwidth, and a Fast-Mode I$^2$C (400 kHz) interface. The gyroscope 116 can also include an embedded temperature sensor and a 2% accurate internal oscillator. An example gyroscope that can be utilized is the ITG-3200 3 IC commercially available from InvenSense, Inc. Other gyroscopes could be utilized.

The displacement sensor 110 can be configured to measure displacement of a moveable tip 124 that is biased by spring or other type of one or more biasing element. For example, the tip 124 can be moveable relative to the body 126 of the device, such the tip can deflect (e.g., displace a distance) commensurate with force applied, such as in response to pressing the tip against a solid surface (e.g., a touchscreen of the tablet computer). The displacement sensor 110 thus can provide an output signal indicative of the displacement along a given axis that is parallel to a longitudinal axis of the device 100. The output signal can be provided to the control system and be stored as displacement data in the memory 106. The control system 102 can be programmed to convert the displacement data to a corresponding pressure value based on the mechanical properties of the biasing spring that is implemented.

The processor 104 can execute instructions to control the sampling of data from the sensors and storage of such data in memory 106. The processor 104 can also control transfer of the stored sensing data from the sensors 112, 114, 116, 110 and 118 to the remote computing machine to which the device has been programmatically registered for communication. For example, instructions associated with each task implemented at the remote machine can be utilized to control communication of the sensed data. Alternatively, the device 100 can transmit sensed data from all its sensors via the communication system 120 continuously in real time or at a defined rate and the requisite data can be extracted from the transmitted data according to application task requirements.

Figure 4:
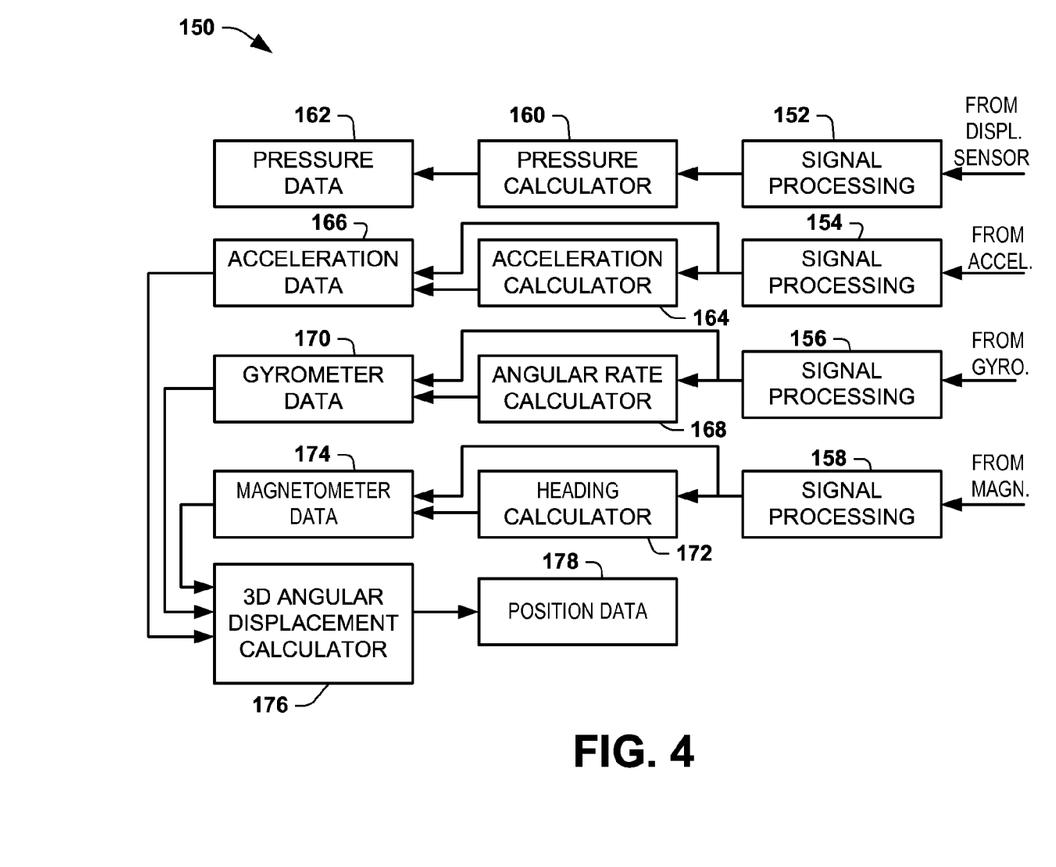
FIG. 4 depicts an example of computer-readable medium programmed to implement processing of sensor data obtained via sensors in a handheld device.

FIG. 4 depicts an example of machine readable instructions that can be stored a non-transitory computer readable medium (e.g., the memory 106 of FIG. 3) and executed by a processing resource (e.g., the processor 104 of FIG. 3) operating on an active stylus device (e.g., the device 14 of FIG. 1, device 100 of FIG. 3). For example, the data and instructions 150 can be utilized for implementing the function and methods and disclosed herein with respect to the handheld device. Signals from each of the respective sensors can be pre-processed by hardware and/or software represented by signal processing blocks 152, 154, 156 and 158. For example, the signal processing 152, 154, 156 and 158 can implement an analog-to-digital conversion, filtering and other processing on the data provided from the respective sensors, such as to provide the data as an n-bit digital signal, where n is positive integer (e.g., n=10) denoting the number of bits for the respective processed signals. While the conversion is discussed as occurring as part of the processing instructions 150, such conversion and other processing could also be implemented within each respective sensor.

As an example, the information from the displacement sensor (e.g., displacement sensor 110 of FIG. 3) can employ the signal processing 152 to smooth the sampled displacement information provided from the displacement sensor. Signal processing can provide processed displacement data to a pressure calculator 160. The pressure calculator 160 can be programmed to compute pressure in terms of force per unit area based on the processed displacement data and the mechanical properties of the biasing utilized to resist displacement of the tip. The pressure calculator 160 can in turn store the computed pressure information as pressure data 162 in the corresponding machine readable medium. Additionally or alternatively, the displacement data can also be stored as the data 162.

The information from the accelerometer can include analog acceleration information for each of a plurality of orthogonal axes of sensitivity, which have a predefined orientation relative to the axis of the stylus. The signal processing 154 thus can convert the analog acceleration information to digital value for acceleration along each of the respective axes as well as perform low pass filtering and normalization of the respective acceleration signals to provide pre-processed acceleration information. An acceleration calculator 164 can be programmed to compute acceleration data in corresponding units based upon the processed acceleration signals and a known range of the accelerometer. The computed acceleration values for each axis as well as the processed acceleration data can be stored as acceleration data 166 in corresponding memory.

Data from the gyroscope can also undergo signal processing 156 to provide processed gyrometer information to an angular rate calculator 168. The angular rate calculator 168 can compute an angular rate of rotation for the stylus device based upon the gyrometer signals that have been processed. The angular rate thus can correspond to an angular velocity measurement for the stylus device about one or more axes. The corresponding angular rate for each such axis as well as an angular position can be computed and stored at the gyrometer data 170. The processed digital gyrometer signals can also be stored as part of the gyrometer data 170.

The magnetometer can provide a magnetic field vector. The magnetic field vector can be pre-processed by signal processing 158 to remove extraneous noise, and the processed magnetometer information can be provided as a digital signal to a heading calculator 172. The heading calculator 172 can be programmed to compute a heading of the stylus device based on the processed magnetometer information. The heading information can be stored as magnetometer data 174 along with the magnetic field data provided by signal processing block 158.

A 3D position vector calculator 176 can be programmed to compute position information (3D angular displacement) along three orthogonal axes (the X, Y, Z axes) of the stylus device. The 3D position calculator can be programmed to compute the angular position based on the acceleration data 166, gyrometer data 170 and magnetometer data 174. For example, the gyrometer data 170 can be integrated to obtain an indication of the displacement. The accelerometer data (e.g., in planes perpendicular to the earth) and magnetometer data 174 (e.g., in the planes parallel to the ground) can be employed to correct for drift in the gyro integration. The resulting position information can be stored as position data and communicated wirelessly to the computing apparatus as disclosed herein. As disclosed herein, each of the pressure data 162, acceleration data 166, gyrometer data 170, magnetometer data 174 and position data 178 can all include respective time stamps that can be synchronized and coordinated with touchscreen data for use in evaluating and analyzing a patient's respective movement disorder.

Figure 5:
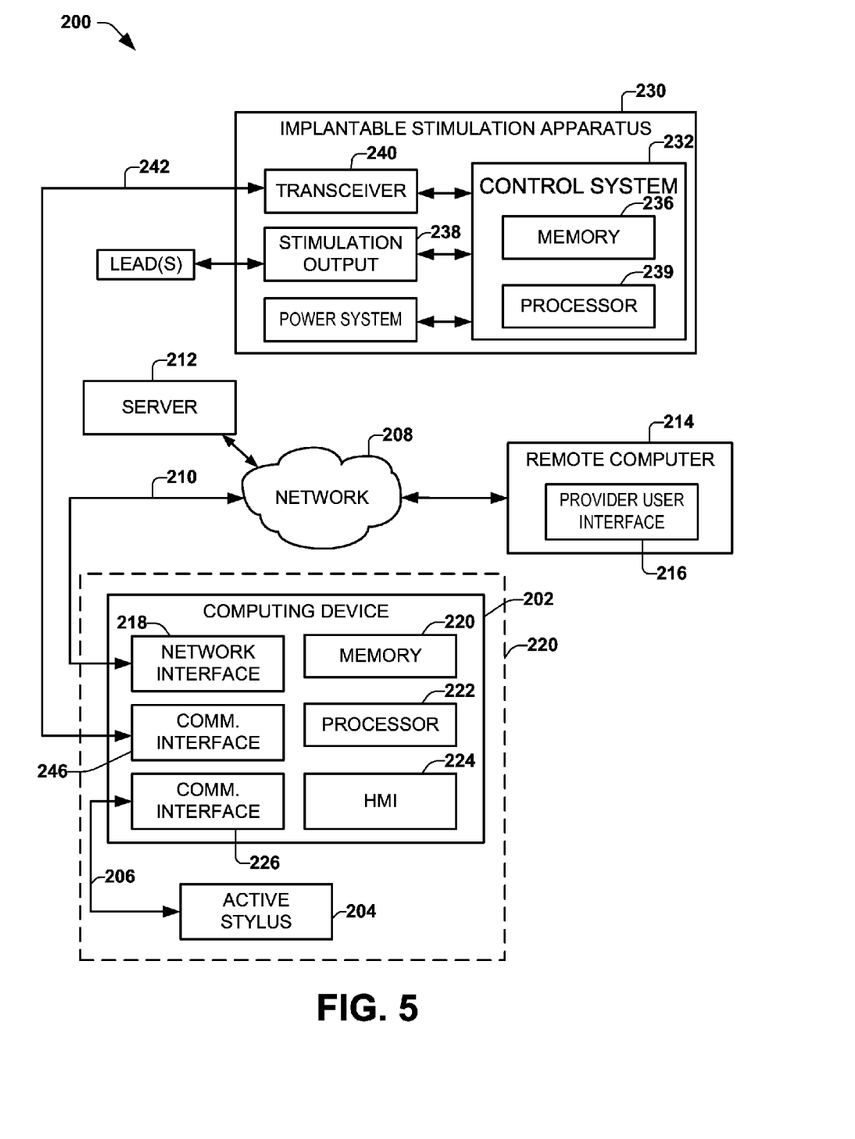
FIG. 5 depicts and example of a system that can facilitate diagnosing and/or treating movement disorders.
Figure 6:
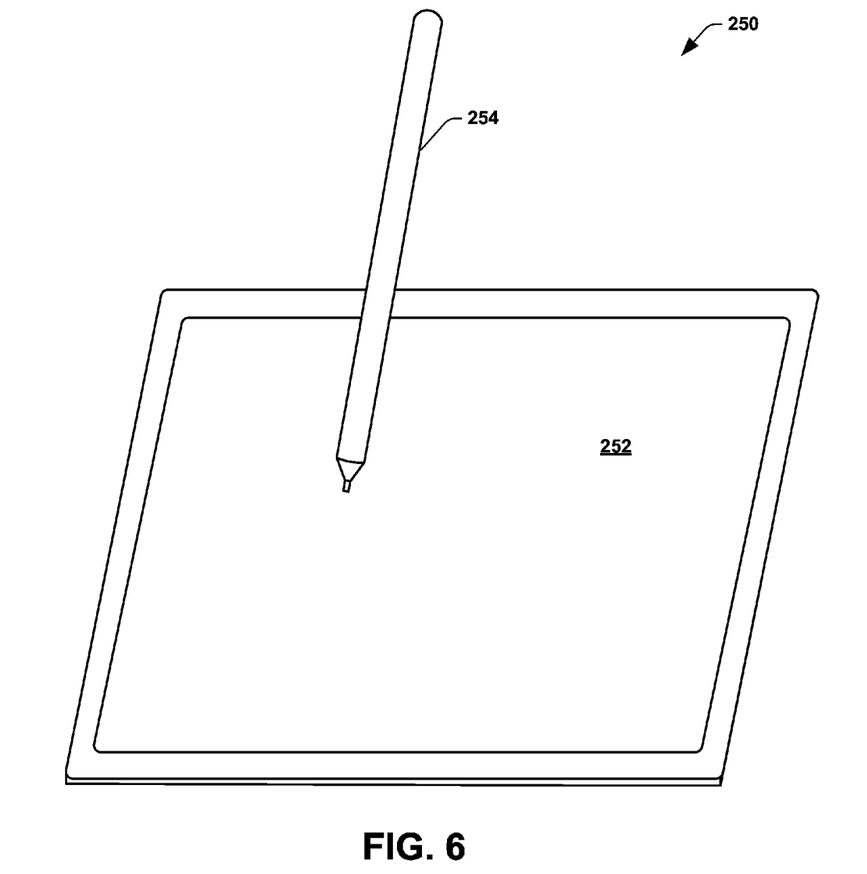
FIG. 6 depicts an example of a handheld apparatus to facilitate evaluation of movement disorders.

FIG. 5 depicts an example of a system 200 that can be implemented for diagnosing and treating movement disorders. In the example of FIG. 5, the system 200 includes a portable computing device 202 and an active stylus 204 which are connected together via communication link 206, such as disclosed with respect to the system 10 of FIG. 1. The computing device 202 can be implemented as a tablet style computer, which includes an HMI 224. The HMI 224 can correspond to a touchscreen as well as can also include one or more buttons or devices (e.g., keyboard, keypad, mouse, touch pad or the like) with which a user can interact with the portable computing device 202. The stylus 204 can be separate from and independently moveable relative to the HMI 224 of the computing device 202, such as for performing the tasks for evaluating movement disorders, as disclosed herein.

The portable computing device 202 can be connected to a network 208 via corresponding communication link 210. The portable computing device can include a network interface 218 that can be utilized for forming the communication link 210 with the network 208. The communication link 210 can be implemented as a wireless link, such as disclosed herein. In other examples, the communications link could be a physical link (e.g., Ethernet or optical fiber) that implements a network protocol for communicating bi-directional data. In this way, the portable computing device 202 can communicate with a server 212 as well as with one or more remote computers 214 via the network 208. The server 212 can be programmed with methods and functions to enable storing data collected by the portable computing device 202 according to the various task disclosed herein for any number of one or more plurality of respective patients. In other example, the server 212 can include the processor, the memory and the communications interface (as described with respect to the computing device 202) and thereby execute instructions corresponding to the tasks disclosed herein. The server 212 thus can generate a graphical user interface that can be presented remotely (e.g., via a browser) for local presentation via the HMI 224 and employ the communications interface to receive the motion and position information from the handheld device as well as the user input data from the HMI. In each example, the server 212 can compile a database of movement analysis data for one or a population of patients.

The server 212 further can include services that can be accessed from the remote computer 214 such as via a provider user interface 216. Additionally, the provider user interface 216 can be configured to communicate with the portable computing device 202 via the network 208. For example, an authorized user can employ the provider user interface 216 for programming or otherwise providing instructions to the computing device 202. The corresponding instructions or other information, for example, can be stored in memory 220 of the portable computing device.

The computing device 202 can also include a processor 222 that can access data and instructions stored in the memory 220. For example, the memory 220 can include instructions corresponding to the tasks 54 of FIG. 2 as well as other functions and methods disclosed herein that can be implemented at a portable computing device such as a tablet computer. The portable computing device also includes a communication interface 226 that enables communication of data between the portable computing device and the active stylus 204 via the link 206, such as disclosed herein. The wireless protocol utilized for the link 206 can be the same or different from the wireless protocol utilized for the link 210.

The system 200 can also include an implantable stimulation apparatus 230, such as an IPG, that can be configured to supply stimulation therapy to a patient. For example, the implantable pulse generator can be implanted in a patient and be connected to one or more leads continuing electrodes strategically located in the patient's anatomy such as within the brain or other part of the nervous system for delivering electrical stimulation. Alternatively or additionally, the stimulation apparatus 230 can be configured to supply optical stimulation to adjacent tissue, such as by providing illumination at one or more specified wavelengths. As yet another example, the stimulation apparatus 230 can deliver chemical stimulation via delivery of a chemical therapeutic agent. Any one or more types of such stimulation (e.g., electrical, optical and/or chemical) can be provided to initiate or inhibit an action potential in surrounding tissue.

To control the application of stimulation to the patient, the stimulation apparatus 230 can include a control system 232 that can include a processor 234 and memory 236. The processor 234 can be configured to access the memory 236 and execute instructions stored therein. The memory 236 can in turn include instructions for controlling operation of the stimulation apparatus 230 including delivery of stimulation provided by an output system 238 based on one or more control parameters. The control parameters and the configuration of the output system 238 can vary depending on the type of stimulation. The stimulation apparatus 230 can also include a power system 244 configured to supply electrical power from an internal battery to the circuitry of the stimulation apparatus. The battery can be rechargeable or disposable.

In order to improve the efficacy of the stimulation provided by the stimulation apparatus 230 to a given patient, one or more parameters stored in the memory 236 can be programmable in response to programming instructions received via a transceiver 240. For example, the transceiver 240 can be configured to communicate with the portable computing device 202 via a communication link 242 between the computing device and the stimulation apparatus 230. As an example, the transceiver 240 can be programmed and/or configured to implement a short range bi-directional wireless communication technology, such as Bluetooth, inductive coupling, or one of the 802.11x protocols. Alternatively, the communications link 242 can be a physical link (e.g., an electrically conductive or optical fiber connection). The computing device 202 can include another communications interface 246 that is configured to communicate with the stimulation apparatus 230 via the communications link 242. The communications can occur using a known protocol or a proprietary protocol, such as for communicating information between the stimulation apparatus and the computing device 202.

By way of further example, one or more series of the tasks can be performed by a patient for a given test session, such as disclosed herein, to acquire corresponding results data for a patient to objectively quantify the patient's movement disorder. Based upon the results data for one or more test sessions, the computing device 202 can be programmed to compute updated control parameters for the stimulation apparatus 230. The computing device can provide the updated control instructions to stimulation apparatus 230 via the link 242, and the parameters can be stored in the memory 236.

For the example of the stimulation apparatus 230 being configured to deliver electrical stimulation, the stimulation output system 238 can be electrically connected to one or more leads that have been strategically positioned in the patient's nervous system, such as an intracranial site for deep brain stimulation. Thus, the control system 232 can control delivery of current or voltage to the leads as well as which leads are activated based upon the control parameters stored in the memory 236. The control parameters can include amplitude, pulse width (e.g., duration), frequency, waveform shape or the like. These and other control parameters can be adjusted based on the results of testing performed by the patient using the computing device and the stylus as disclosed herein.

Thus as part of the monitoring and treatment program for a given patient, the computing device 202 can be programmed to adjust and update the stimulation parameters over time based on the testing that is performed by a given patient. After the stimulation parameters have been adjusted based upon the results data, further testing can be performed by the patient over a period of time (e.g., one or more days or a week). The test results that have been obtained following the update or adjustment to the stimulation parameters can be analyzed by corresponding movement analysis methods of the portable computing device 202 to determine if any further adjustments are required or if an adequate (e.g., a target) level of improvement in the movement disorder has been achieved. In addition to employing the results data from testing, as disclosed herein, patient clinical data can also be combined with the test data. The clinical data can include an indication of a duration that the patient has had a given disorder, the patient's age, weight or other factors that may affect a patient's test. In this way, the computing device can employ close loop control based on feedback from the testing to fine tune and maintain stimulation parameters for a given patient.

Additionally or alternatively, the results data for a given patient can be viewed and evaluated by a healthcare provider, such as via the provider user interface 216. The corresponding provider, having sufficient authorization, can set updated stimulation parameters that can be sent via the network 208 to the portable computing device 202 and stored in the memory 220. Control methods stored in the memory 220 can in turn send the updated stimulation parameters via the communications interface 246 to program the stimulation apparatus 230. The updated stimulation parameters can be stored in the local memory 236 for use in controlling subsequent delivery of therapy to the patient. Thus, as disclosed herein, the method of updating and adjusting the stimulation parameters can be fully automated, be fully manual or implement a combination of manual and automated modifications of the stimulation parameters stored in the memory 236.

The stimulation parameters can be initially calibrated via a predetermined set of tasks performed in a programming session at an in-person meeting with a provider. Another set of tasks, which can be the same or different from the programming session can then be performed remotely by the patient in the absence of the provider, the results from which can be utilized to update the stimulation parameters. As a further example, test results for a given patient can be aggregated over a period of time and evaluated in total to ensure sufficient reliability of the measurements of the patient's movement disorder as well as to evaluate the level of function that a given patient can achieve as described by the results data.

It will thus be appreciated that the system 200 of FIG. 5 as well as other systems and methods disclosed herein facilitate distance-based monitoring, such as through telemedicine. Additionally, since the testing can be self-administered, it enables a care provider (e.g. a physician) to monitor the patient's condition over time to determine the course of disease and the effect of intervention for each of a plurality of patients. For example, the results and acquired data can be transferred directly to the patient's physicians or other care providers to assess progress over a period of time without requiring in-office visits. In examples where the subject includes the implantable stimulation apparatus 230, the provider and/or computer implemented methods operating remotely (e.g., the server 212 or remove computer 214) or within locally in the computing device 202 can be programmed to set one or more stimulation parameters based on the results and other data acquired over time.

To provide additional context, FIG. 4 depicts an example of a system 250 that can be utilized to implement the testing methods disclosed herein. The system 250 includes a tablet computer 252, which includes a touchscreen HMI. The system 250 also includes an active stylus 254 that is separate from and independently moveable relative to the touchscreen of the tablet computer 252, such as for performing the tasks for evaluating movement disorders, as disclosed herein.

As will be appreciated by those skilled in the art, portions of the invention may be embodied as a method, data processing system, or computer program product. Accordingly, these portions of the present invention may take the form of an entirely hardware embodiment, an entirely software embodiment, or an embodiment combining software and hardware. Furthermore, portions of the invention may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments of the invention are described herein with reference to flowchart illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

Figure 7:
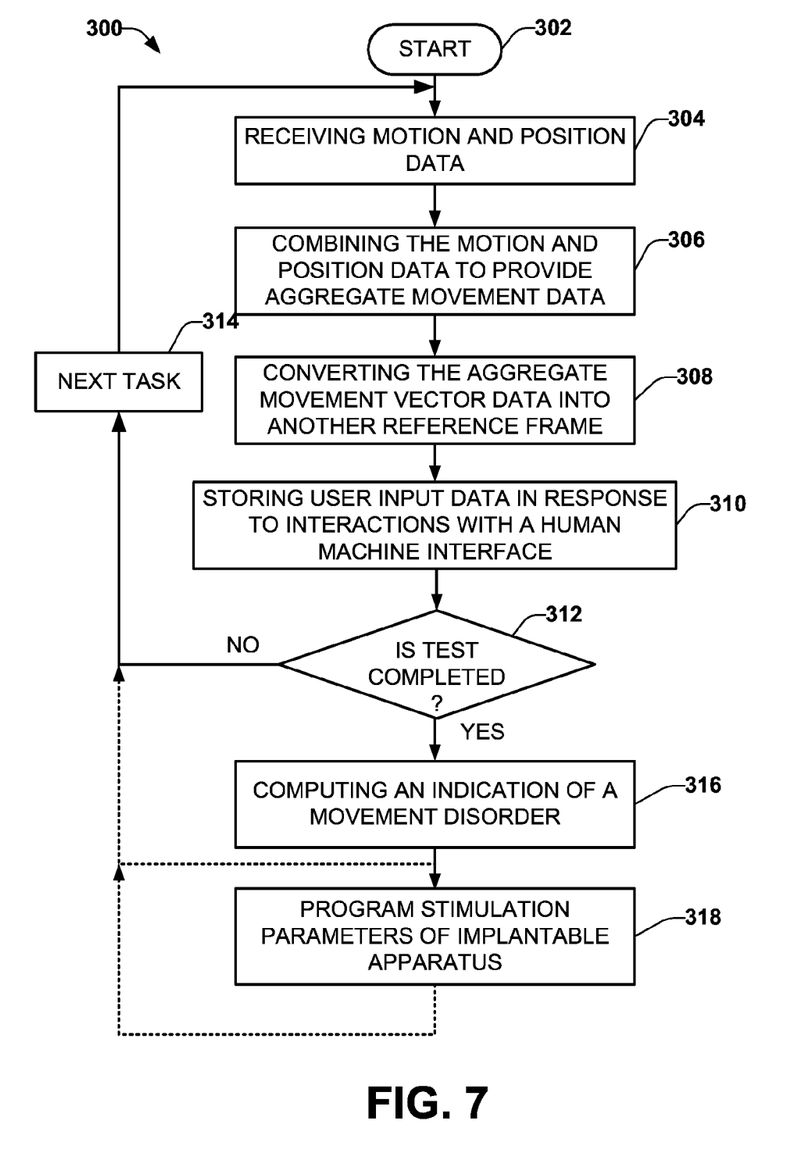
FIG. 7 depicts an example of a method for evaluation of movement disorders.

In view of the foregoing structural and functional features described above, an example method will be better appreciated with reference to FIG. 7. While, for purposes of simplicity of explanation, the example method of FIG. 7 is shown and described as executing serially, it is to be understood and appreciated that the present examples are not limited by the illustrated order, as some actions could in other examples occur in different orders and/or concurrently from that shown and described herein. The method can be implemented as computer readable instructions, such as can be stored in a non-transitory medium, such as a memory device. The instructions in the medium may be executed by a processing unit.

The method 300 begins at 302 such as in connection with initiating a testing session, which can include any number of one or more predetermined tasks, such as disclosed herein. Each task can begin at a start time that can be indicated via an HMI (e.g., HMI 12 of computing device 23 FIG. 1 or HMI 224 of FIG. 5), such as can include an audible and/or visual cue. Each task can also involve a handheld device (e.g., device 14 of FIG. 1 or stylus 204 of FIG. 5) that is separately moveable from the HMI. At 304, the method includes receiving motion and position data, such as via a communications link. For instance, the motion and position data can be generated based on motion and position sensed by sensors (e.g., sensors 112, 114, 116 and/or 110 of FIG. 3) of a handheld device during the predetermined task. At 306, the motion and position data can be combined (e.g., by data aggregation 64 of FIG. 2) to provide aggregate movement data describing multi-dimensional movement of the handheld device. At 308, the aggregate movement vector data can be converted (e.g., by relative movement calculator 67 of FIG. 3) into relative movement data corresponding to position and motion of the handheld device with respect to a reference frame of the human machine interface. At 310, user input data can be stored (e.g., in memory of the computing device) in response to user interactions detected by the human machine interface during the at least one predetermined task.

At 312 a determination is made as to whether the test is completed. If the test is not completed, the method can proceed to 314 to load the next task. From 314, the method can repeat 304-310 for such task. If the test is completed, the method proceeds to 316. At 316, an indication of one or more movement disorder can be calculated (e.g., by any of the calculators of movement analysis 62 of FIG. 2) based on the relative movement data and the user input data.

In some examples, where a subject has an implantable stimulation apparatus (e.g., the apparatus 230 of FIG. 5) the method can proceed to 318 for programming the implantable stimulation apparatus based on the indication of the at least one movement disorder. The indication of a movement disorder can be from one test or from a plurality of different test sessions. As disclosed herein, for example, a plurality of test sessions can be performed to occur at different times, and each of 304-316 repeated for each of the plurality of test sessions. Where multiple tests have been performed over a period of time, the indication of the at least one movement disorder can be computed based on the relative movement data and the user input data from at least two of the plurality of test sessions, such as two or more most recent sessions.

In view of the foregoing, the approach disclosed herein affords an opportunity for extended monitoring of patients that might have different degrees of symptom severity depending on the time of the day and/or depending on the timing between one dose of medication and the next. When examined by clinicians patients are seen in various degrees of symptom severity, providing a physician with only a snapshot of symptom burden during the day. Clinicians rely on patient information regarding the severity of symptoms at other times. The simplicity of this approach thus allows patients to record symptom severity several times a day, including times of average, worse, best symptom control. This information can be provided to and reviewed by clinicians in aggregate and provide a better objective picture of symptom severity over a period of time.

Additionally, while the approach disclosed herein can be employed to quantify symptoms for Parkinson's disease, the approach is equally applicable to other movement disorders and symptoms. For example, in addition to Parkinson's disease, the apparatus, each of the systems and methods disclosed herein are equally applicable to evaluating other movement disorders, such as can include akathisia, akinesia, associated Movements (e.g., Mirror Movements or Homolateral Synkinesis), athetosis, ataxia, ballismus, hemiballismus, bradykinesia, cerebral palsy, chorea, Sydenham's chorea, rheumatic chorea, Huntington's disease, dystonia, Geniospasm, myoclonus, metabolic general unwellness movement syndrome (MGUMS), mirror movement disorder, paroxysmal kinesigenic dyskinesia, WittMaack-Ekboms disease, spasms, stereotypic movement disorder, stereotypy, Tardive dyskinesia, tic disorders, tremors and Wilson's disease.

What have been described above are examples. It is, of course, not possible to describe every conceivable combination of components or methodologies, but one of ordinary skill in the art will recognize that many further combinations and permutations are possible. Accordingly, the invention is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A system comprising:
    memory to store computer executable instructions and data; and
    a processor configured to access the memory and execute the computer executable instructions which comprise:
        a data aggregator to combine motion and position data from a plurality of sensors into an aggregate movement data describing multi-dimensional movement of a handheld device;
        a relative movement calculator to convert the aggregate movement data into relative movement data corresponding to a reference frame of a human machine interface, the human machine interface being separate from the handheld device; and
        a calculator to compute an indication of a movement disorder based on the relative movement data and user input data that is stored in the memory, the user input data being generated in response to user interaction between the handheld device and the human machine interface.

2. The system of claim 1, wherein the human machine interface comprises a touchscreen, the processor controlling a graphical user interface provided on the touchscreen over a plurality of tasks.

3. The system of claim 2, further comprising a computing device that includes the touchscreen, the processor generating the graphical user interface on the touchscreen according to user interface instructions stored in the memory.

4. The system of claim 1, wherein the calculator comprises a tremor calculator to characterize the movement disorder as a tremor based on the relative movement data and the user input data.

5. The system of claim 1, wherein the calculator comprises a bradykinesia calculator to characterize the movement disorder as bradykinesia based on the relative movement data and the user input data.

6. The system of claim 1, wherein the calculator comprises a dexterity calculator to characterize the movement disorder based on an indication of dexterity determined based on the relative movement data and user input data.

7. The system of claim 1, wherein the instructions further comprise a task control configured to control the human machine interface over each of a plurality of separate tasks, the motion and position data obtained from the plurality of sensors and the user input data obtained from the human machine interface during each of the plurality tasks being stored in the memory.

8. The system of claim 1, wherein the handheld device comprises an active stylus, the plurality of sensors being integrated into the active stylus.

9. The system of claim 8, wherein the plurality of sensors comprises at least two of a multidimensional accelerometer, a multidimensional magnetometer and a multidimensional gyroscope.

10. The system of claim 9, wherein the plurality of sensors of the handheld device further includes a displacement sensor configured to measure displacement of a moveable tip that extends from an end of the active stylus, the instructions further comprising a pressure calculator being programmed to compute an indication of force corresponding to the interaction between the active stylus and the human machine interface based on the measured displacement, the indication of the movement disorder being determined based on the relative movement data, the indication of force and user input data that is stored in the memory.

11. The system of claim 9, wherein the handheld device further comprises an angular displacement calculator to compute multi-dimensional angular displacement of the handheld device based on the multidimensional accelerometer, the multidimensional magnetometer and the multidimensional gyroscope.

12. The system of claim 1, further comprising a communications interface configured to receive the motion and position data from the handheld device, the motion and position data representing position and motion of the handheld device during a time interval corresponding to each of a series of tasks.

13. The system of claim 12, wherein the communications interface is a wireless communication interface, the handheld device being registered with the communications interface to enable the motion and position data to be received and stored in the memory in real time.

14. The system of claim 12, wherein the user input data represents interaction with the human machine interface during each of the series of tasks, the motion and position data being synchronized in time with the user input data for each of the series of tasks.

15. The system of claim 12, further comprising a server that includes the processor, the memory and the communications interface, the server further being programmed to generate a graphical user interface that is provided via a network to a computing device that includes the human machine interface, the computing device further being programmed, in real time of data acquisition during at least one of the tasks, to provide instructions or feedback to the user concurrently with the at least one of the tasks.

16. The system of claim 1, wherein the memory and the processor reside in a computing device that includes the human machine interface, the system further comprising a implantable stimulation apparatus configured to generate an output based on at least one stimulation parameter, the computing device being configured to program the at least one stimulation parameter based on the indication of the movement disorder.

17. The system of claim 16, wherein the system further comprises a remote computer configured to communicate with the computing device via a network, the remote computer providing instructions to the computing device to program the at least one stimulation parameter in response to a user input.

18. A system comprising:
an active stylus comprising:
a kinematic sensing system that includes a plurality of sensors configured to provide motion and position data about the stylus;
a computing device comprising:
a human machine interface configured to generate user input data in response to interaction between the stylus and the human machine interface;
instructions executable by a processor to perform a method comprising:
combining the motion and position data from the plurality of sensors into aggregate movement data describing multi-dimensional movement of the stylus; and
computing an indication of a movement disorder based on the aggregate movement data and the user input data.

19. The system of claim 18, wherein the system further comprises an implantable stimulation apparatus configured to generate an output based on at least one stimulation parameter, the computing device being configured to program the at least one stimulation parameter based on the indication of the movement disorder via a communications link between the computing device and the implantable stimulation apparatus.

20. The system of claim 19, wherein the system further comprises a remote computer configured to communicate with the computing device via a network, the remote computer providing instructions to the computing device to program the at least one stimulation parameter.

21. The system of claim 18, wherein the kinematic sensing system comprises at least two of a multidimensional accelerometer, a multidimensional magnetometer and a multidimensional gyroscope.

22. The system of claim 21, wherein the stylus further comprises a displacement sensor configured to measure displacement or pressure of a moveable tip that extends from an end of the stylus according to the interaction between the active stylus and the human machine interface, the indication of the movement disorder being determined based on the aggregate movement data, the measured displacement or pressure and the user input data.

23. The system of claim 18, wherein the computing device further comprises a wireless communications interface configured to receive the motion and position data from the stylus, the motion and position data representing real-time motion and position of the stylus during each of a series of tasks.

24. The system of claim 23, wherein the user input data represents interaction with the human machine interface during each of the series of tasks, the motion and position data being synchronized in time with the user input data for each of the series of tasks.

25. A method comprising
receiving, via a communications link, motion and position data based on motion and position sensed by sensors of a handheld device during at least one predetermined task;
combining the motion and position data to provide aggregate movement data describing multi-dimensional movement of the handheld device;
converting the aggregate movement data into relative movement data corresponding to position and motion of the handheld device with respect to a reference frame of a human machine interface that is separate from the handheld device;
storing user input data in response to user interactions detected by the human machine interface during the at least one predetermined task; and
computing an indication of at least one movement disorder based on the relative movement data and the user input data.

26. The method of claim 25, further comprising programming an implantable stimulation apparatus based on the indication of the at least one movement disorder.

27. The method of claim 25, wherein the at least one predetermined task comprises a plurality of test sessions that occur at different times, and each of the receiving, combining, converting and generating is repeated for each of the plurality of test sessions, the indication of the at least one movement disorder being computed based on the relative movement data and the user input data from at least two of the plurality of test sessions.

* * * * *